(12) United States Patent
Koulikov

(10) Patent No.: US 7,810,376 B2
(45) Date of Patent: Oct. 12, 2010

(54) MITIGATION OF GAS MEMORY EFFECTS IN GAS ANALYSIS

(75) Inventor: Serguei Koulikov, Mountain View, CA (US)

(73) Assignee: Picarro, Inc., Sunnyvale, CA (US)

(*) Notice: Subject to any disclaimer, the term of this patent is extended or adjusted under 35 U.S.C. 154(b) by 152 days.

(21) Appl. No.: 11/983,128

(22) Filed: Nov. 6, 2007

(65) Prior Publication Data
US 2009/0113988 A1 May 7, 2009

(51) Int. Cl.
*G01N 7/02* (2006.01)
(52) U.S. Cl. ........................................ 73/23.31
(58) Field of Classification Search ................ 73/23.2, 73/23.21, 23.31, 1.06, 23.29, 23.32
See application file for complete search history.

(56) References Cited

U.S. PATENT DOCUMENTS

| | | | |
|---|---|---|---|
| 5,454,860 A | 10/1995 | Zhu | |
| 5,661,038 A | 8/1997 | Brenna et al. | |
| 5,763,763 A * | 6/1998 | Kato et al. | 205/781 |
| 5,780,710 A * | 7/1998 | Murase et al. | 73/1.06 |
| 5,841,022 A | 11/1998 | Hase | |
| 5,877,406 A * | 3/1999 | Kato | 73/23.31 |
| 5,948,964 A * | 9/1999 | Kato | 73/23.31 |
| 6,044,689 A * | 4/2000 | Yoshida et al. | 73/31.03 |
| 6,214,208 B1 * | 4/2001 | Ando et al. | 205/781 |
| 6,310,340 B1 | 10/2001 | Rettinghaus | |
| 7,122,152 B2 * | 10/2006 | Lewis et al. | 422/50 |

* cited by examiner

*Primary Examiner*—John Fitzgerald
(74) *Attorney, Agent, or Firm*—Lumen Patent Firm

(57) ABSTRACT

The gas absorption/adsorption memory effect in gas analysis can be reduced by controlling gas flow conditions such that the partial pressure of the analyte of interest is held constant, if the measured analyte concentration is within a predetermined range. Keeping the analyte partial pressure constant is helpful for mitigating the memory effect because changes in analyte absorption/adsorption rates tend to be driven by changes in analyte partial pressure. The memory effect can also be mitigated by performing concentration measurements at two or more different gas flow conditions, and employing a mathematical model to estimate true concentration and "memory effect" contributions to measured concentrations at one or more of the flow conditions. The mathematical model can be based on an assumption that the true analyte concentration is independent of flow rate or pressure, while the "memory effect" contribution to measured concentration is inversely proportional to flow rate or pressure.

5 Claims, 3 Drawing Sheets

MITIGATION OF GAS MEMORY EFFECTS IN GAS ANALYSIS

FIELD OF THE INVENTION

This invention relates to gas handling for gas analysis.

BACKGROUND

In gas analysis, it is frequently desirable to monitor a time-dependent concentration of an analyte in a sample gas. In such situations, the "memory effect" is a well-known problem in the art, in which the measured analyte concentration can undesirably depend on the past history of the measurement system. For example, if the analyte concentration starts out high and then abruptly decreases to a much lower level, the gas analysis sensor may provide erroneously high analyte readings for some time after the analyte concentration decreases. The memory effect is especially severe for sticky analytes, such as water vapor or ammonia.

Various physical processes can contribute to the memory effect. For example, the analyte can be adsorbed onto surfaces of the sample chamber and/or gas delivery system. The analyte can also be dissolved (i.e., absorbed) into parts of the sample chamber and/or delivery system.

Several methods of mitigating or avoiding this memory effect have been considered in the art. For example, in U.S. Pat. No. 5,661,038, isotopic analysis of Hydrogen is improved by providing a water trap to remove memory effects due to water vapor. In U.S. Pat. No. 6,310,340, memory effects from a leakage valve part of the gas delivery system are mitigated by using this part of the system as a barrier gas line and/or as a pumping line. In U.S. Pat. No. 5,841,022, two parallel input systems are employed in alternating succession, such that the gas input system that is idle at any point in time can be purged to remove absorbed/adsorbed gas.

In U.S. Pat. No. 5,454,860, mitigation of a somewhat different memory effect is considered in a system in which the sample is provided as a liquid and made gaseous for analysis. The mitigation approach taken in this reference is to actively pump out fluid from the system, thereby reducing memory effects due to lingering fluid.

However, a need remains for improved mitigation of the memory effect associated with gas absorption/adsorption in the gas handling system. This need is especially acute in cases where the analyte of interest is a sticky gas that tends to have significant adsorption/absorption, such as ammonia or water vapor.

SUMMARY

The gas absorption/adsorption memory effect in gas analysis can be reduced by controlling gas flow conditions such that the partial pressure of the analyte of interest is held constant, provided the analyte concentration presented for analysis is within a predetermined range. Keeping the analyte partial pressure constant is helpful for mitigating the memory effect because changes in analyte absorption/adsorption rates tend to be driven by changes in analyte partial pressure. The analyte partial pressure can be held constant by altering the total pressure in the gas sample chamber and/or by admitting a known fraction of inert gas to the sample chamber, where the inert gas is known not to include the analyte of interest.

The memory effect can also be mitigated by performing concentration measurements at two or more different gas flow rate conditions, and employing a mathematical model to estimate true concentration and "memory effect" contributions to measured concentrations at one or more of the flow rate conditions. The mathematical model can be based on an assumption that the true analyte concentration presented for analysis is independent of flow rate, while the "memory effect" contribution to the observed concentration is inversely proportional to flow rate. Another option is to base the mathematical model on an assumption that the true analyte concentration is independent of total pressure in the sample chamber, while the "memory effect" contribution to the observed concentration is inversely proportional to total pressure in the sample chamber.

DETAILED DESCRIPTION

Figure 1:
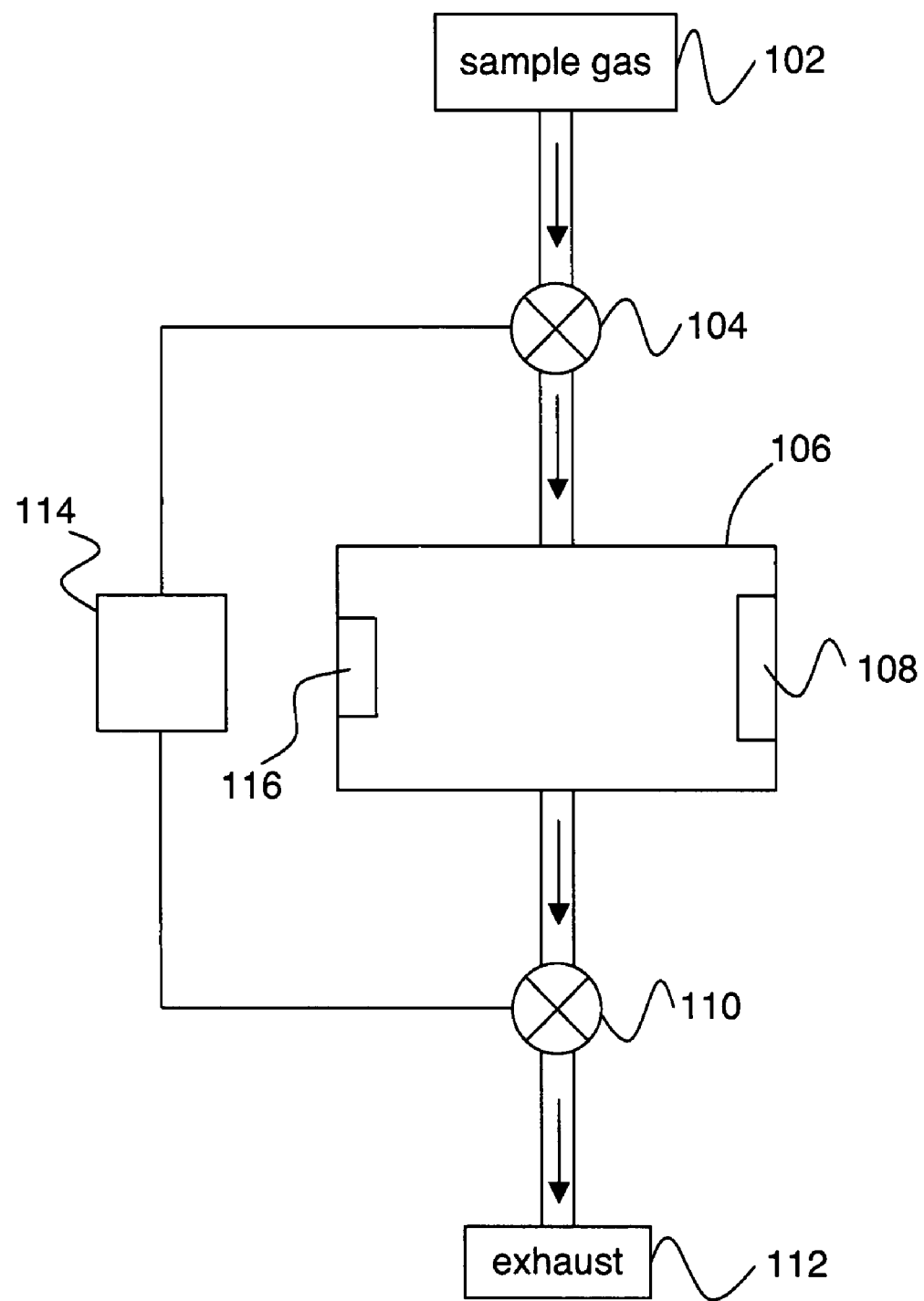
FIG. 1 shows a gas handling system according to a first embodiment of the invention.

FIG. 1 shows a gas handling system according to a first embodiment of the invention. The example of FIG. 1 includes a sample chamber 106 capable of admitting sample gas for analysis from a sample gas source 102. A gas analyte sensor 108 is operatively connected to sample chamber 106 and is capable of measuring analyte concentration or analyte partial pressure in the sample gas. A pressure sensor 116 measures the total gas pressure in sample chamber 106. Knowledge of the total gas pressure in sample chamber 106 allows analyte concentration to be determined from analyte partial pressure, or vice versa. Typically, sensor 108 directly provides a partial pressure measurement. A gas flow controller is also included, which is capable of altering the analyte partial pressure in sample chamber 106. In this example, the gas flow controller includes a controller 114 connected to an inlet flow controller 104 and an outlet flow controller 110. Gas emitted from outlet flow controller 110 is received by an exhaust subsystem 112.

Practice of the invention is not significantly affected by implementation details pertaining to sensor 108, sample chamber 106, or the gas flow controller (e.g., 104, 110, and 114). Accordingly, embodiments of the invention are applicable to any kind of gas sensor 108, and any kind of sample gas handling apparatus. The reduced memory effect provided by embodiments of the invention is especially beneficial for ultra-sensitive gas sensors 108, including but not limited to sensors based on: cavity ring-down spectroscopy (CRDS); other forms of cavity-enhanced absorption spectroscopy (CEAS) such as (off-axis) integrated cavity output spectroscopy (ICOS, OA-ICOS); evanescent wave spectroscopy such as using an optical fiber, micro-resonator (whispering gallery mode resonator), or CRDS (EW-CRDS); adsorption-reflection spectroscopy; and non-optical detection methods.

In this example, the memory effect is mitigated by configuring the gas flow controller to maintain the partial pressure of the analyte being monitored substantially constant by altering the total pressure, provided the analyte concentration in the gas from sample gas source 102 is within a predetermined control range. For example, suppose the nominal operating total pressure of a gas analyzer for monitoring ammonia is 200 Torr and the nominal ammonia concentration being monitored is 10 ppbv (i.e., the nominal ammonia partial pressure $P_a$ is $2 \times 10^{-6}$ Torr). A control range of 5 ppbv to 20 ppbv can be selected (i.e., predetermined), such that the total pressure in sample chamber 106 is maintained at $P_t = 2000/M_c$ Torr if 5 ppbv≦$M_c$≦20 ppbv by the gas flow controller, where $M_c$ is the ammonia concentration of gas from sample gas source 102 in ppbv. In this example: if $M_c$=10 ppbv, the total pressure is 200 Torr; if $M_c$=5 ppbv, the total pressure is 400 Torr; and if $M_c$=20 ppbv, the total pressure is 100 Torr. In all three cases, the ammonia partial pressure $P_a$ is $2\times10^{-6}$ Torr (i.e., it is held constant). If the concentration in gas from the sample gas source falls outside the predetermined range, the total pressure can be set to some nominal or default value (i.e., 200 Torr in this example). In cases in which the analyte concentration in gas from the sample gas source falls outside the predetermined control range, mitigation of the memory effect does not occur.

Arranging the system such that the partial pressure of the analyte of interest is held constant advantageously mitigates the memory effect, since changes in absorption/adsorption rates tend to be driven by changes in partial pressure. By reducing or eliminating such changes in analyte partial pressure, a state of dynamic equilibrium can be reached or approached, where the net absorption/adsorption rate of the analyte is relatively low. By reducing this net absorption/adsorption rate, the memory effect is advantageously reduced.

Figure 2:
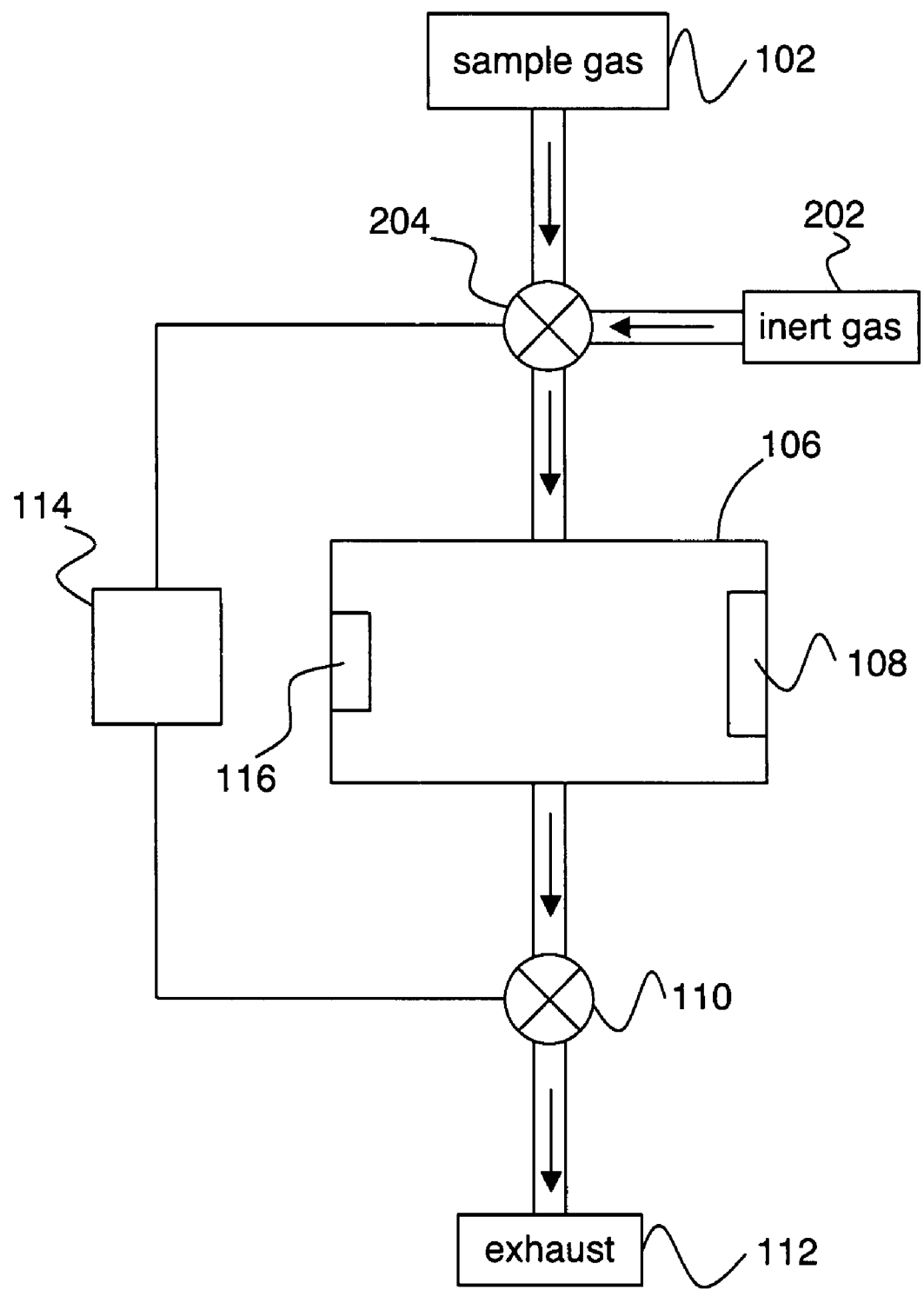
FIG. 2 shows a gas handling system according to a second embodiment of the invention.

Other methods of keeping the partial pressure constant can also be employed in practicing embodiments of the invention, such as mixing a known fraction of inert gas with the sample gas in the sample chamber. FIG. 2 shows a gas handling system according to an embodiment of the invention where such mixing is employed. This embodiment is similar to the embodiment of FIG. 1, except that the gas flow controller in the example of FIG. 2 includes a mixer 204 capable of providing a mixture of the sample gas and an inert gas from inert gas source 202 to sample chamber 106.

This mixing can be performed with a volume sample gas fraction, R=sample/(sample+inert), set by the gas flow controller according to an algorithm that maintains the analyte partial pressure substantially constant, provided the analyte concentration in the sample gas falls within a predetermined control range. It is important that the inert gas not include the analyte of interest in its composition. The inert gas preferably does not include any species that could erroneously register as the analyte of interest in sensor 108. In this case, the concentration of analyte in the gas provided by sample gas source 102 equals $P_a/(R\times P_t)$.

For example, suppose a nominal ammonia partial pressure for ammonia monitoring is $10^{-6}$ Torr at a fixed total pressure of 100 Torr. If the ammonia concentration in the sample gas is 20 ppbv, R should be 0.5 to keep the ammonia partial pressure equal to $10^{-6}$ Torr. If the ammonia concentration in the sample gas is 80 ppbv, R should be 0.125 to keep the ammonia partial pressure equal to $10^{-6}$ Torr.

In this example, the predetermined control range is 20 ppbv to 80 ppbv, and the fraction of sample gas in the sample chamber, R, is maintained at $R=10/M_c$ if 20≦$M_c$≦80 by the gas flow controller, where $M_c$ is the ammonia concentration in ppbv in the sample gas provided by source 102. If the ammonia concentration of the sample gas is outside this range, then the sample gas fraction may be set to some nominal value, e.g. ½. The inert gas fraction is 1-R. One feature of this example is that the operating pressure in sample chamber 106 is held constant as the sample gas fraction is varied.

It is also possible to hold the partial pressure constant by both altering the total pressure in the sample chamber and altering a known fraction of inert gas in the sample chamber. By employing both techniques together, the range of measured analyte concentrations (i.e., the control range) over which the analyte partial pressure can be held constant can be increased. In this case, the concentration of analyte in the sample gas provided by gas source 102 equals $P_a/(R\times P_t)$, where both R and $P_t$ can vary in chamber 106.

In the preceding embodiments of the invention, it is important to note that the analyte concentration in chamber 106 may or may not be the same as the analyte concentration in the gas provided by sample gas source 102. In embodiments where the total pressure $P_t$ is varied to maintain the analyte partial pressure $P_a$ in chamber 106 constant, the analyte concentration $M_c$ (by volume) in the gas provided by gas source 102 is given by $M_c=P_a/P_t$, which is also the analyte concentration in chamber 106. In contrast, for embodiments where the sample gas fraction R is varied to maintain the analyte partial pressure $P_a$ in chamber 106 constant, the analyte concentration $M_c$ (by volume) in the gas provided by gas source 102 is given by $M_c=P_a/(R\times P_t)$, while the analyte concentration in chamber 106 is given by $P_a/P_t$. It is important to provide concentration results pertaining to the sample gas as provided by source 102, since this is the primary quantity of interest for measurement applications.

Figure 3:
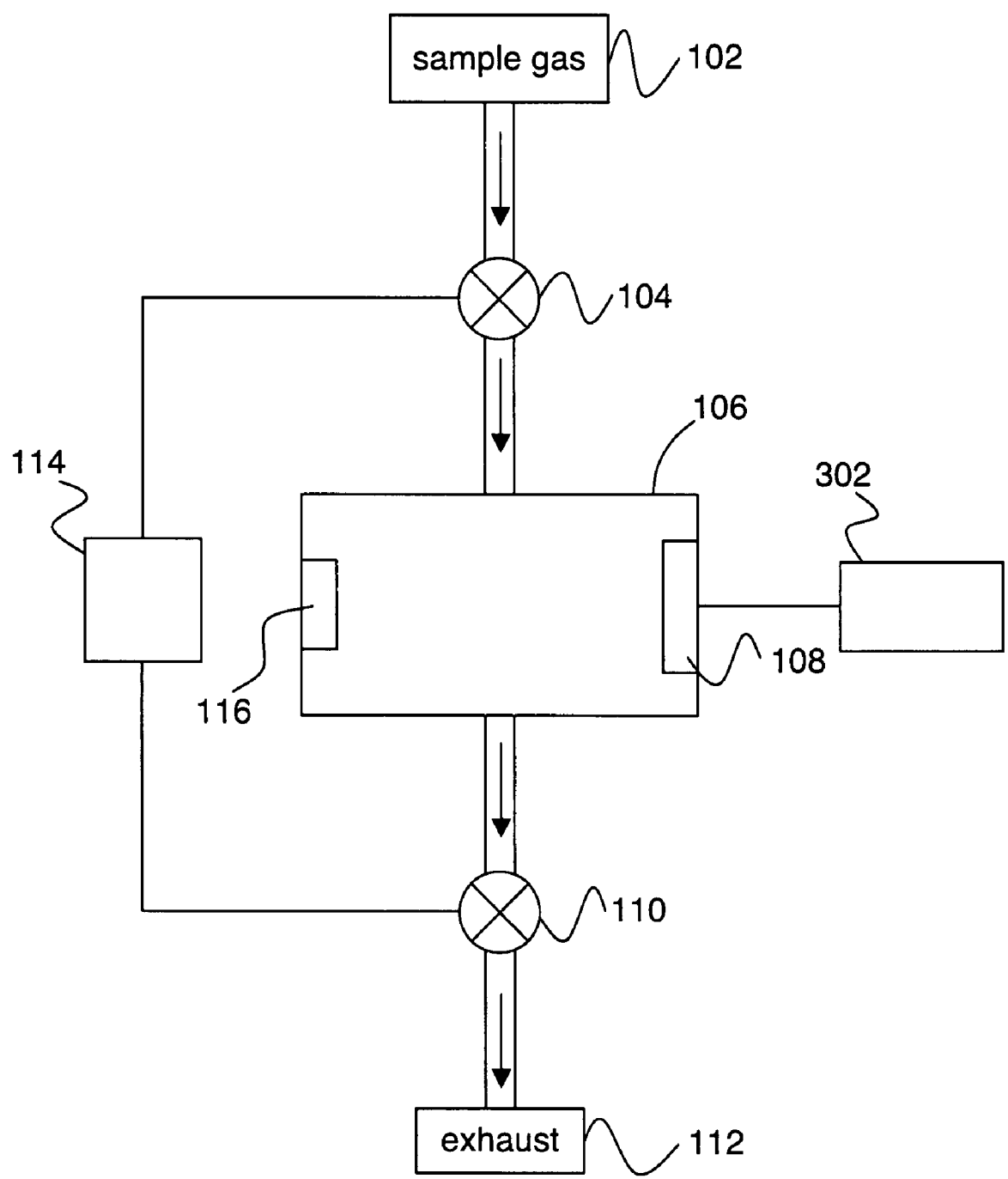
FIG. 3 shows a gas handling system according to a third embodiment of the invention.

The preceding embodiments of the invention relate to mitigation of gas memory effects by holding the analyte partial pressure constant. Other embodiments of the invention relate to memory effect mitigation by taking measurements at two or more different gas flow conditions, and employing a mathematical model to estimate true analyte concentration from the measurements. FIG. 3 shows a gas handling system according to an embodiment of the invention in which such processing is performed.

The example of FIG. 3 is similar to the example of FIG. 1, except that a processor 302 is connected to sensor 108 on FIG. 3. Processor 302 is capable of providing estimates for true analyte concentration of the sample gas source 102 and memory effect contribution to the analyte concentration in chamber 106 based on measurements performed at two or more distinct gas flow conditions. Gas flow conditions can be described in terms of gas flow parameters, such as pressure, flow rate, and temperature in the sample chamber.

Processor 302 can be any combination of hardware and/or software. Determination of the true and "memory effect" analyte concentrations is based on a mathematical model, which can be provided to the process as a corresponding algorithm. Various mathematical models can be employed in practicing embodiments of the invention.

For example, the mathematical model can be based on assuming the true analyte concentration is independent of flow rate and that the "memory effect" contribution to analyte concentration is inversely proportional to flow rate, F, while keeping the total pressure, $P_t$, constant. Using this method, the concentration $M_s$ measured by sensor 108 is the sum of the true analyte concentration, $M_a$, and the contribution from the "memory effect," $M_m=A_m/F$, where $A_m$ is a measure of the rate of desorption of analyte. $M_s$ is a function of F: $M_s(F)=M_a+M_m=M_a+A_m/F$. Both $M_a$ and $A_m$ can be determined from measurements of $M_s$ at two or more flow rates, F.

Suppose 10 ppbv of analyte is measured at flow rate $F_1$, and 6 ppbv of analyte is measured shortly thereafter at flow rate $2F_1$. Application of this mathematical model to this numerical example gives the following equations: $M_a+A_m/F_1=10$ ppbv and $M_a+A_m/2F_1=6$ ppbv, which have solution $M_a=2$ ppbv and $A_m=8(ppbv)F_1$. From these measurements, and the assumptions made in the model, it follows that the true analyte concentration is 2 ppbv for this example. Additionally, at flow rate $F_1$, the "memory effect" contribution to the concentration is 8 ppbv.

As another example, the mathematical model can be based on assuming the true analyte concentration is independent of total pressure and that the "memory effect" analyte concentration is inversely proportional to total pressure, $M_m = B_m/P_t$. In this case, $M_s$ is a function of $P_t$: $M_s(P_t) = M_a + M_m = M_a + B_m/P_t$. Suppose 10 ppbv of analyte is measured at total pressure $P_1$, and 7 ppbv of analyte is measured shortly thereafter at pressure $2P_1$. Application of this mathematical model to this numerical example gives the following equations: $M_a + B_m/P_t = 10$ ppbv and $M_a + B_m/2P_t = 7$ ppbv, which have solution $M_a = 4$ ppbv and $B_m = 6(\text{ppbv})P_1$. From these measurements, and the assumptions made in this model, it follows that the true analyte concentration is 4 ppbv for this example, and the "memory effect" contribution to the concentration at total pressure $P_1$ is 6 ppbv.

Since the "memory effect" is out of equilibrium in at least one of the measurements of $M_s$ in each of the above two examples, the quantities $A_m$ and $B_m$ change over time, approaching zero until the flow condition is changed, at which time they assume new values according to the new flow condition and again decay in time. The decay can usually be accurately modeled by an exponential function. If significant decay of $A_m$ or $B_m$ occurs between measurements of $M_s$, the equations in the above two paragraphs should be modified to include the effect of the decay. The decay rate (if it is exponential) may be taken as a predetermined fixed value, or determined from measurements of $M_s$ in time.

The invention claimed is:

1. Apparatus for measuring a time variable concentration of an analyte in a sample gas, the apparatus comprising:
    a sample chamber capable of admitting said sample gas for analysis;
    a sensor operatively connected to said sample chamber and capable of measuring a concentration of said analyte in said sample gas;
    a gas flow controller capable of altering a partial pressure of said analyte in said sample chamber;
    wherein said gas flow controller is configured to maintain said partial pressure substantially constant, provided said measured concentration is within a predetermined control range;
    wherein said gas flow controller maintains said partial pressure substantially constant by mixing a known fraction of inert gas with said sample gas in said sample chamber while holding a total pressure of said sample chamber constant, wherein said inert gas is known to not include said analyte.

2. Apparatus for measuring a time variable concentration of an analyte in a sample gas, the apparatus comprising:
    a sample chamber capable of admitting said sample gas for analysis;
    a sensor operatively connected to said sample chamber and capable of measuring a concentration of said analyte in said sample gas;
    a gas flow controller capable of altering a partial pressure of said analyte in said sample chamber;
    wherein said gas flow controller is configured to maintain said partial pressure substantially constant, provided said measured concentration is within a predetermined control range;
    wherein said gas flow controller maintains said partial pressure substantially constant by:
    i) altering a total pressure in said sample chamber; and
    ii) mixing a known fraction of inert gas with said sample gas in said sample chamber, wherein said inert gas is known to not include said analyte.

3. A method of measuring a time variable concentration of an analyte in a sample gas, the method comprising:
    admitting said sample gas to a sample chamber for analysis;
    measuring a concentration of said analyte in said sample gas with a sensor operatively connected to said sample chamber;
    controlling a partial pressure of said analyte in said sample chamber with a gas flow controller to maintain said partial pressure substantially constant, provided said measured concentration is within a predetermined control range;
    wherein said measuring a concentration of said analyte in said sample gas comprises:
    measuring a chamber concentration of said analyte in gas in said sample chamber; and
    determining said concentration of said analyte in said sample gas from said measured chamber concentration;
    wherein said controlling said partial pressure of said analyte in said sample chamber comprises mixing a known fraction of inert gas with said sample gas such that a sample gas fraction in said chamber is $R < 1$.

4. The method of claim 3, wherein said measured chamber concentration is given by $M_{chamber}$, and wherein said determining said concentration of said analyte in said sample gas comprises providing $M_{chamber}/R$ as said determined analyte concentration in said sample gas.

5. A method of measuring a time variable concentration of an analyte in a sample gas, the method comprising:
    admitting said sample gas to a sample chamber for analysis, wherein said sample gas in said sample chamber has one or more gas flow parameters;
    measuring concentrations of said analyte in said sample chamber with a sensor at two or more distinct values of said gas flow parameters;
    providing a mathematical memory effect model which can provide an estimate for true analyte concentration from said two or more concentration measurements;
    providing said estimate of said true analyte concentration as an output.

* * * * *